United States Patent [19]
Danielsson

[11] 3,934,576
[45] Jan. 27, 1976

[54] CENTRAL VENOUS CATHETER SYSTEM
[75] Inventor: Curt Aslov Danielsson, Borlange, Sweden
[73] Assignee: AB Sundsvalls Specialprodukter, Sundsvall, Sweden
[22] Filed: Nov. 14, 1973
[21] Appl. No.: 415,753

[30] Foreign Application Priority Data
Nov. 17, 1972 Sweden.............................. 14941/72

[52] U.S. Cl. ........................ 128/2.05 D; 128/214 R
[51] Int. Cl.² ........................................... A61B 5/02
[58] Field of Search ...... 128/2.05 R, 2.05 D, 214 R, 128/214.2

[56] References Cited
UNITED STATES PATENTS

| 2,600,324 | 6/1952 | Rappaport................. 128/2.05 D X |
| 2,910,981 | 11/1959 | Wilson et al..................... 128/214 A |
| 3,413,970 | 12/1968 | Rockwell....................... 128/2.05 D |
| 3,435,819 | 4/1969 | Reynolds et al. ............... 128/2.05 D |
| 3,495,585 | 2/1970 | Halligan et al.................. 128/2.05 D |

FOREIGN PATENTS OR APPLICATIONS
1,024,410  3/1966  United Kingdom.............. 128/214.4

Primary Examiner—Dalton L. Truluck
Attorney, Agent, or Firm—Silverman & Cass, Ltd.

[57] ABSTRACT

Apparatus for safe puncturing of a central vein having a flexible catheter and a one-way valve connected thereto. A flexible extension tube connects the catheter with a multiway valve for connecting venous pressure means and supply means to the patient.

6 Claims, 4 Drawing Figures

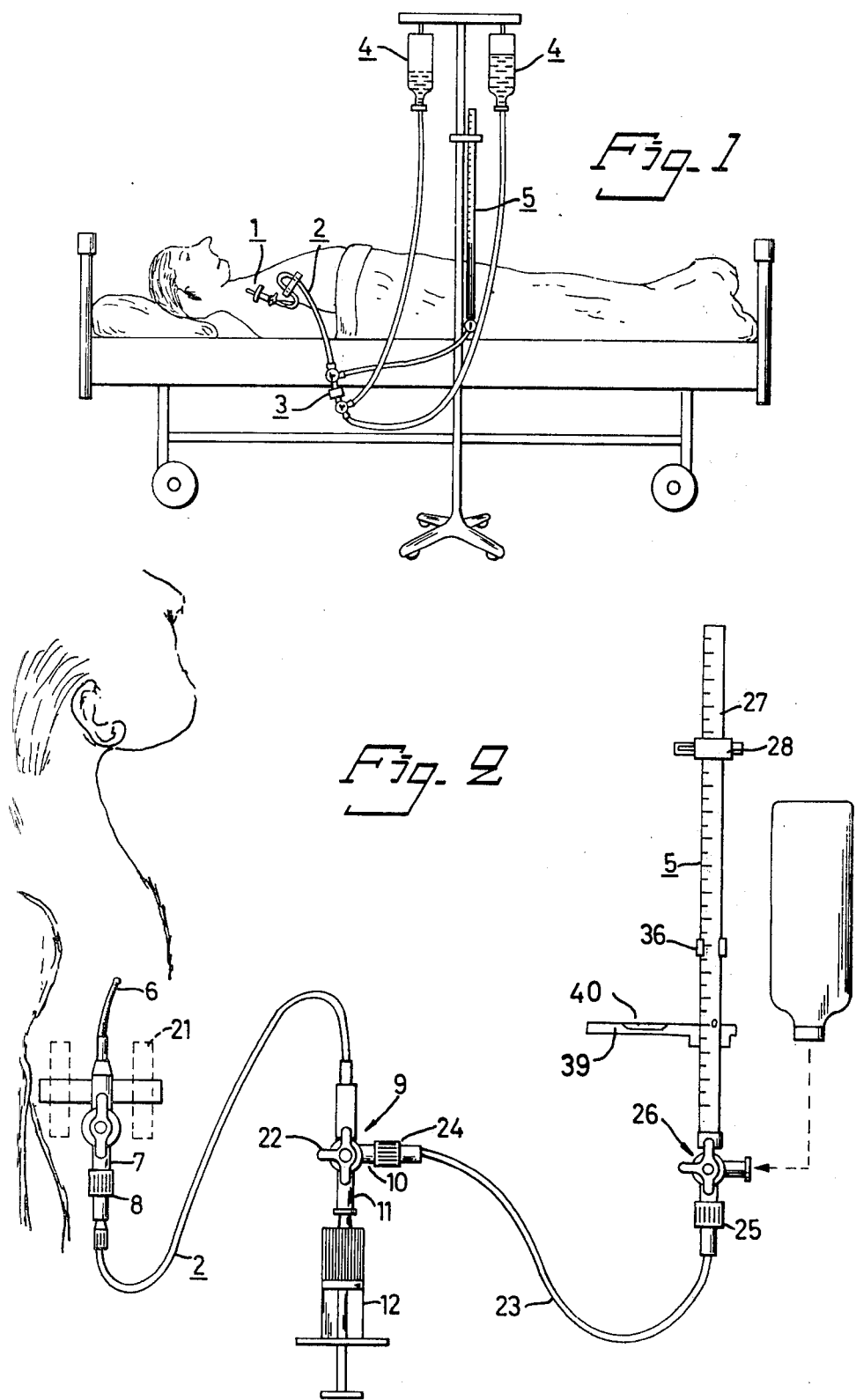

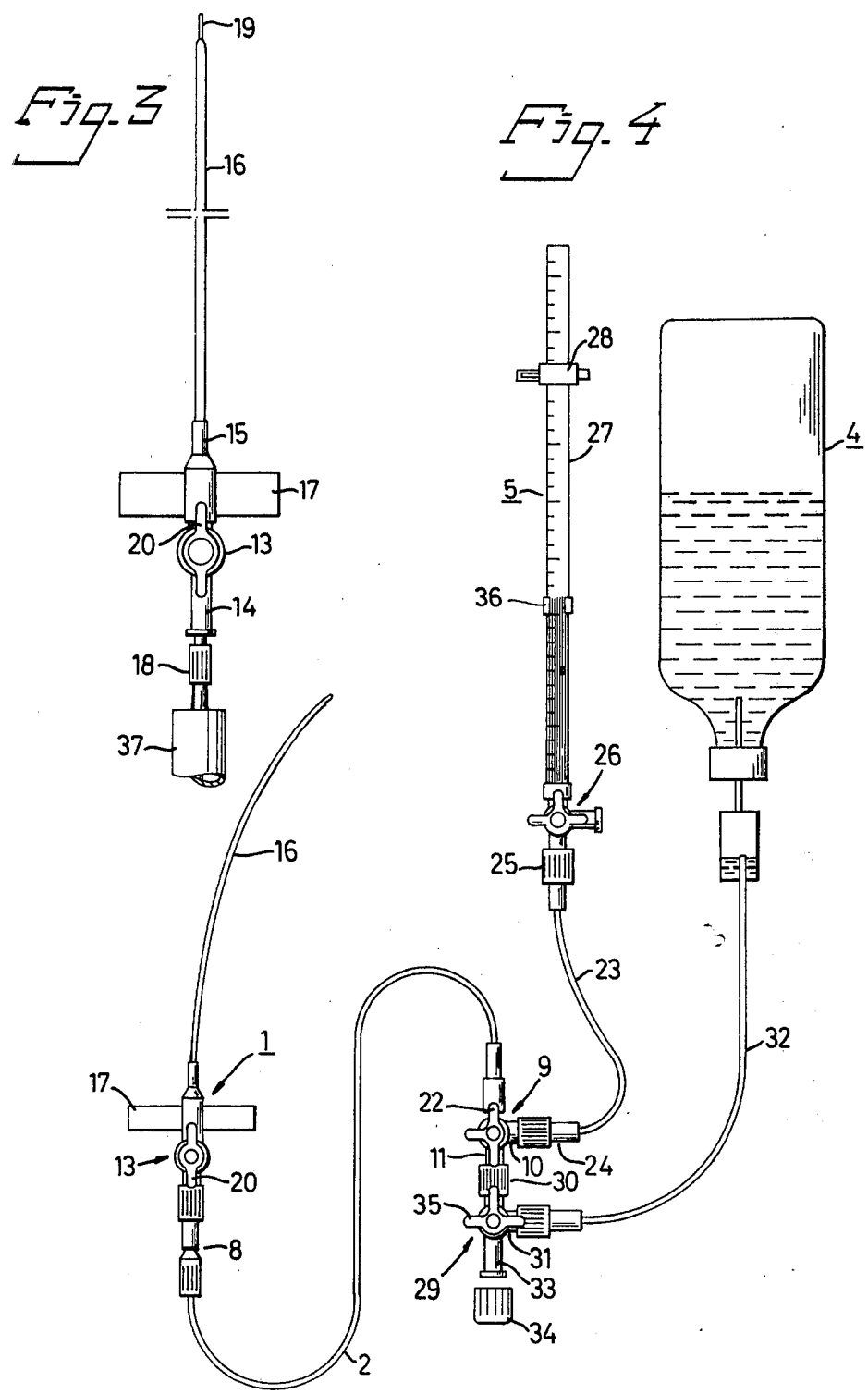

CENTRAL VENOUS CATHETER SYSTEM

BACKGROUND OF THE INVENTION

The present invention relates to apparatus for the use of a central venous catheter preferably by puncturing of the vena subclavia in the human body.

DESCRIPTION OF THE PRIOR ART

Great advantages have been obtained by the method of administering liquid and nourishment into the patient through a central venous catheter means, as for instance applied to vena subclavia. Such a venous catheter means is used for measuring the central venous pressure, giving an indication of the liquid status of the human body during supply of liquid or nourishment into the patient in large amounts.

In spite of the advantages, this method has not become commonly used due to certain problems and disadvantages in priorly known venous catheters systems. The problems of applying a central venous catheter by puncture of the vena subclavia are mainly caused by the fact that there is a subpressure prevalent in the vena subclavia, and, therefore, the risk of drawing air into the patient with subsequent air emboli is always to be considered. When puncturing the vena subclavia or changing infusion substance or accessories it is, therefore, of the greatest importance that this is done while keeping in mind the subpressure that is present in the vein and in the venous catheter system.

A priorly known venous catheter system comprises an infusion cannula having a catheter means which is mounted in sealed condition in an adapter formed with a through bore, and in which the cannula extends somewhat outside the catheter. When puncturing the vena subclavia the patient is placed in a particular position, whereupon the cannula is filled with a suitable liquid by means of a syringe, and at the time when the vena subclavia is punctured blood is drawn into the syringe, and the cannula is drawn out at the same time the outlet is closed so that no air is allowed to enter the catheter. The catheter and the adapter are attached directly to the chest of the patient with the aid of tape or the like. If the venous pressure is to be measured or liquid or nourishment is to be administered to the patient, a flexible tube is connected directly between the venous pressure gauge or the bottle of liquid or nourishment and the venous catheter, whereby all air is carefully removed from the connection point. It is to be noted that only one connection may be established at the time. When providing this connection, the venous catheter will certainly be rotated or turned, which may cause the patient pain and create a risk that the catheter which is usually made of a thin plastic material is broken. There is also the risk that air is sucked into the vein due to the prevailing subpressure in the vein. This is also the case when changing over from measuring the venous pressure to infusing some substance. Further, there is also always a risk of infection when working close to the point of puncture. This also applies to a situation wherein an injection is given via the central venous catheter by means of a syringe.

In order to avoid the disadvantages of the previously known venous catheter means having an adapter, the adapter has been substituted by a one-way valve or a three-way valve having two outlets, wherein two different accessories may be connected to the venous catheter means, for instance, a venous pressure meter to one of the outlets and a liquid or nourishment pipe to the other outlet. The risk of introduction of air is, however, still greater with the three-way valve means, and the risk of buckling or twisting of the catheter when turning the adjustment tap of the three-way valve is also great and so is the risk of contamination of the point of puncture.

The present invention intends to overcome the said disadvantages or priorly known venous catheter systems and to provide a system in which the risk of air emboli, the risk of buckling of the catheter and the risk of contamination at the point of puncture are eliminated or at least greatly reduced, and in which a venous pressure meter and one, two or more infusion medium supplies may be connected simultaneously.

SUMMARY OF THE INVENTION

The invention is based on the idea that all adjustable connection means are removed from the point of puncture, and in its most simple form the invention comprises an infusion cannula having a flexible catheter which is mounted in a one-way valve and wherein the cannula may be pulled out, and a joint tube which is connected to the one-way valve and which carries in its free end several connection means for simultaneous and alternative connection of a venous pressure meter, an injection syringe, and different liquid media.

BRIEF DESCRIPTION OF THE DRAWINGS

FIG. 1 shows diagrammatically the apparatus according to the invention connected to a patient in bed, wherein two infusion media and a venous pressure meter are connected simultaneously to the venous catheter system;

FIG. 2 illustrates in greater detail, an embodiment of the invention, in which a venous pressure meter and an injection syringe are connected simultaneously to the venous catheter system;

FIG. 3 shows the venous catheter with the cannula introduced therein, illustrating the method of puncturing a vein; and FIG. 4 shows an embodiment of the venous catheter system according to the invention including means for connecting several infusion or measuring devices.

DESCRIPTION OF THE PREFERRED EMBODIMENTS

The apparatus according to the invention generally comprises a valve catheter 1 connected to a flexible extension tube 2. At the other end of the extension tube 2, a connection means 3 is provided for one or more drop bottles (vitrum guttificans) and a venous pressure meter 5. The valve catheter is applied to the vena subclavia just under the collarbone, for the purpose of continuously or intermittently gauging the central venous pressure, supplying large amounts of liquids during long periods or frequently taking venous samples. As pointed out above there is a subpressure in the vena subclavia, and a risk that air may be sucked into the said vein during the puncture and application of the catheter, or adjustment or substitution of connection parts adjacent the valve catheter. There is also a risk that the catheter is buckled or twisted if changes of connections are frequently made at the valve catheter. For this reason and in order to avoid too close a contact with the point of puncture and the risk of infection caused thereby, the valve catheter according to the invention is provided with the flexible extension tube 2, which at one end is connected in sealed relationship to the connection hose 7 of the valve catheter, such as by means of an aperture cone and tap cone lock. A preferred embodiment of such an aperture cone and tap cone lock is illustrated by connection 8 and known under the trademark LUER-LOK. The other end of extension tube 2 is provided with a multiway cock, such as a three-way cock 9 having two connections 10 and 11, for a venous pressure meter 5, and an infusion device or an injection syringe 12 for direct injection through the extension tube and the catheter 1.

As best seen in FIG. 3, the valve catheter comprises a one-way valve 13 having a connection 14 of the above-noted LUER-LOK type and an outlet connection 15 in which a catheter 16 of a thin and flexible material is mounted in sealed condition. The valve is provided with attachment wings 17 whereby the valve may be attached directly to the patient. A cannula 18 extends through the valve and the catheter and the tip 19 thereof projects somewhat out of the catheter 16. The valve 13 is of the conventional tapvalve type, and the valve tap is provided with a handle in the form of two wings 20 indicating the flow direction through the valve tap. In the position shown in FIG. 3 the valve is open, such that the cannula 18 extends straight through the valve tap, and when the cannula is withdrawn from the catheter 16, a flow may occur through the valve catheter. This is the normal position for infusion or gauging the venous pressure. The attachment wings 17 of the valve catheter are attached by means of a tape or the like 21 directly to the patient.

The flexible extension tube 2 may be of any suitable material which is flexible and resistant against the stresses which may occur. At one end it is formed with connection means of the LUER-LOK type for a locking and sealing engagement with the connection 7 of the valve catheter. At the other end, the extension tube 2 is provided with a three-way valve 9. The three-way valve 9 is also of the tap-valve type, wherein the tap handle is indicating the flow direction through the valve. At one connection 10 of valve 9, the venous pressure means or meter 5 is connected via a pressure conduit 23 which at both ends is provided with connection means 24 and 25 of the LUER-LOK type. The venous pressure means 5 may, if desired, be provided at the lower end with a further three-way valve 26 of the same type as the valve 9, and the meter is, in conventional manner, formed as an open and graduated pipe 27 having an attachment clamp by means of which the pipe may be fastened at any suitable place and level in relation to the patient. Normally, the venous pressure meter is located with its zero point on the same horizontal level as the center of the heart of the patient.

As indicated in FIG. 2, an injection syringe 12 may be connected to the connection 11 of the three-way valve 9 for direct injection through the valve 9, the extension tube 2 and the valve catheter 1. In this situation, the valve handle 22 is adjusted such that the intermediate handle pinpoints to the left, i.e., the venous pressure meter is disconnected. Without such disconnection there is a risk that the infusion medium is forced into the venous pressure meter.

In the embodiment shown in FIG. 4, a three-way valve 29 which may be of the same type as the valve 9, has an aperture cone connection means 30 and is coupled to connection 11, and to a connection 31 of the three-way valve 29. A dropping bottle 4 is coupled over the flexible tube 32 to connection 31.

For injecting two different media simultaneously, means for supplying the second medium may be connected to the free connection 33 of the three-way valve 29. Also, an injection syringe may be applied in the same way as shown in FIG. 2. If the free connection 33 is not used, a protection cover 34 is screwed on for preventing penetration of air and contamination. Also, the three-way valve 29 is formed with a three-armed handle 35 indicating the flow direction through the valve. FIG. 4 also illustrates that the venous pressure meter pipe 27 is formed with a clip 36 which is movable along the pipe for marking the latest venous pressure measured.

It is of great importance that the zero point of the venous pressure meter is adjusted in relation to the patient or rather the heart of the patient, and for this purpose, the venous pressure meter may have a sight means 39 for facilitating the adjustment of the zero point thereof to the correct vertical level. The sight means 39 may, as diagrammatically shown in FIG. 2, be provided with a water level 40 for horizontal adjustment of the sight means and a subsequent vertical positioning of the venous pressure meter. The sight means may be a mechanical device or it may be an electric lamp ejecting a narrow beam so that the pressure meter may with great accuracy be correctly positioned in the vertical direction.

In applying the central venous catheter, the procedure may be as follows: A conventional injection syringe 37 containing some suitable liquid is connected to the valve catheter 1 and the cannula 18 is filled with such liquid, whereupon the vena subclavia is punctured at the point 6. At the same time blood is aspirated through the cannula 18 into the syringe 19 so as to prevent introduction of air, which may otherwise occur due to the subpressure in the vein. While still aspirating, the cannula needle is withdrawn, and when the needle tip passes the valve 13, the valve is closed by turning the handle 20 by 90°. The cannula 18 is completely withdrawn, and in place thereof the flexible extension tube 2 is connected by means of the lock connection 8, the venous pressure meter 5 is connected by means of the lock connection 24, and one or more dropping bottles 4 may be connected over connections 11 or 31 and 33 respectively. The venous pressure meter 5 is adjusted to the correct vertical position in relation to the patient, and upon making sure that all air is removed from tubes and connections, the zero point is adjusted at the venous pressure meter, which may be done by means of the bottle of liquid connected to the valve 26. When gauging the venous pressure, the valve 9 is opened so as to connect the venous pressure meter 5 with the valve catheter 1, and in case the venous pressure meter is provided with the valve 26 this valve is also opened as indicated in FIG. 2. The venous pressure meter will thereby continuously give the pressure of the vein. If it is now desired to introduce a liquid to the patient, the venous pressure meter is disconnected at the valve 9, as indicated in FIG. 4, and the valve 29 is opened such that a flow will occur from the dropping bottle 4 into the patient via the valve catheter 1.

As indicated in FIG. 1, the connection means 3 is located on a level substantially lower than that of the valve catheter 1, whereby the subpressure prevailing in the vein is compensated. Even if a false connection or false adjustment of the valves has been made such that the flexible extension tube 2 is opened towards air, this would not create any risk to the patient, since the subpressure in the vein is compensated. Depending on what action is desired, the valves 9 and 29 are adjusted, while the valve 13 is kept open until the central venous catheter is removed. Since the venous pressure meter is continuously connected to the catheter system, it is possible to check at any time and very quickly the venous pressure and thereby to obtain very rapidly an indication of the liquid status of the patient. This can be done without the risk of air emboli, since the subpressure in the vena subclavia is compensated. There is also no risk of buckling or twisting of the catheter tube since it is kept fixed by the wings 17 taped against the patient and also since there is no need to touch the valve catheter 1 anytime subsequent to the connection of the extension tube 2. Also, in the system according to the invention, the risk of infection at the point of performance has been reduced, since there is no handling close to this point but rather at the outer end of the extension tube 2. By providing the valve catheter 1 with a one-way valve the risks of false adjustment of the tap and penetration of air are avoided.

What it is desired to secure by Letters Patent of the United States is:

1. Apparatus for safe puncturing of a central vein such as a vena subclavia, comprising: a flexible catheter of thin material having at one end a tip and at the other end a one-way valve connected thereto, a flexible extension tube having a first end and a second end, the first end thereof sealingly connectible to the other end of the catheter and the one-way valve, a multiway-valve connected to the second end of the flexible tube and including connections for venous pressure, injection syringe means and dropping supply means, a retractable cannula connectible to the other end of the catheter through the one-way valve in lieu of said extension tube and capable of extending through the one-way valve and the catheter and having a tip portion for projecting from the tip of the catheter, and a venous pressure meter connected to the venous pressure connection of said multiway-valve.

2. Apparatus as set forth in claim 1, in which the connection between the flexible extension tube and the one way valve and catheter is a sealing lock connection of aperture cone and tap cone type.

3. Apparatus as set forth in claim 1, in which the venous pressure meter comprises a graduated pipe including a multiway-valve mounted in the bottom thereof, wherein said last noted valve may be connected to a bottle for filling and calibrating the venous pressure meter.

4. Apparatus as set forth in claim 3, in which the venous pressure meter is constructed to be vertically displaceable relative to an attachment clamp for vertical adjustment of the graduated pipe in relation to the position of the patient, and further including a displaceable clip for indicating the latest measured venous pressure.

5. Apparatus as set forth in claim 4, in which the venous pressure meter comprises means for adjusting the graduated pipe in vertical position in relation to the patient.

6. Apparatus as set forth in claim 5, in which the means for adjusting the graduated pipe comprises a sight and water level means for adjusting the horizontal position of the sight.

* * * * *

UNITED STATES PATENT OFFICE
CERTIFICATE OF CORRECTION

PATENT NO. : 3,934,576
DATED : January 27, 1976
INVENTOR(S) : CURT ASLOV DANIELSSON It is certified that error appears in the above-identified patent and that said Letters Patent are hereby corrected as shown below:

On the title page, block [73], change the Assignee from

"AB SUNDSVALLS SPECIALPRODUCKTER, SUNDSVALL, SWEDEN" to

-- DAMECO MEDICAL PRODUCTS AB, BORLANGE, SWEDEN --.

Signed and Sealed this twenty-seventh Day of April 1976

[SEAL]

Attest:

RUTH C. MASON
Attesting Officer

C. MARSHALL DANN
Commissioner of Patents and Trademarks